United States Patent
Labyed et al.

(10) Patent No.: US 11,006,928 B2
(45) Date of Patent: May 18, 2021

(54) SOUND SPEED IMAGING USING SHEAR WAVES

(71) Applicant: Siemens Medical Solutions USA, Inc., Malvern, PA (US)

(72) Inventors: Yassin Labyed, Maple Valley, WA (US); David Duncan, Renton, WA (US); Seungsoo Kim, Sammamish, WA (US); Stephen Rosenzweig, Bellevue, WA (US); Liexiang Fan, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1500 days.

(21) Appl. No.: 15/040,457

(22) Filed: Feb. 10, 2016

(65) Prior Publication Data
US 2017/0224308 A1    Aug. 10, 2017

(51) Int. Cl.
*A61B 8/08* (2006.01)
*G01S 7/52* (2006.01)
*A61B 8/00* (2006.01)

(52) U.S. Cl.
CPC .............. *A61B 8/485* (2013.01); *A61B 8/08* (2013.01); *A61B 8/5207* (2013.01); *A61B 8/5223* (2013.01); *G01S 7/52022* (2013.01); *G01S 7/52042* (2013.01); *G01S 7/52049* (2013.01); *A61B 8/461* (2013.01)

(58) Field of Classification Search
CPC ........................................................ A61B 8/00
USPC ........................... 73/597; 407/407, 437–472
See application file for complete search history.

(56) References Cited

U.S. PATENT DOCUMENTS

| 6,368,279 | B1  | 4/2002 | Liu |
| 8,784,318 | B1* | 7/2014 | Napolitano ......... G01S 7/52049 600/443 |
| 2002/0010398 | A1* | 1/2002 | Bonnefous ............... A61B 8/08 600/442 |
| 2011/0112404 | A1  | 5/2011 | Gourevitch |
| 2013/0131511 | A1* | 5/2013 | Peterson .............. A61B 5/0048 600/438 |
| 2015/0087976 | A1  | 3/2015 | Fan |
| 2015/0094579 | A1  | 4/2015 | Fan et al. |
| 2015/0148673 | A1  | 5/2015 | Yoshikawa et al. |

(Continued)

FOREIGN PATENT DOCUMENTS

| CN | 104434216 A | 3/2015 |
| EP | 2649944 | 10/2013 |
| JP | 2013512026 A | 4/2013 |

(Continued)

OTHER PUBLICATIONS

Bercoff et al., "Supersonic Shear Imaging: A New Technique for Soft Tissue Elasticity Mapping", IEEE Transactions on Ultrasonics, Ferroelectrics, and Frequency Control, vol. 51, No. 4, Apr. 2004. pp. 396-409. (Year: 2004).*

(Continued)

*Primary Examiner* — James M Kish (57) ABSTRACT

Shear wave propagation is used to estimate the speed of sound in a patient. An ultrasound scanner detects a time of occurrence of a shear wave at each of multiple locations. The difference in time of occurrence, given tissue stiffness or shear velocity, is used to estimate the speed of sound for the specific tissue of the patient.

19 Claims, 5 Drawing Sheets

(56) References Cited

U.S. PATENT DOCUMENTS

| | | | |
|---|---|---|---|
| 2015/0173718 A1* | 6/2015 | Tabaru | A61B 8/08 600/438 |
| 2017/0032519 A1* | 2/2017 | Thornton | A61B 8/4416 |

FOREIGN PATENT DOCUMENTS

| | | |
|---|---|---|
| KR | 20150037689 A | 4/2015 |
| WO | 2016019053 | 2/2016 |

OTHER PUBLICATIONS

Napolitano et al., "Sound speed correction in ultrasound imaging", available online Jul. 20, 2006. Ultrasonics 44. pp. e43-e46. (Year: 2006).*

Cho et al., "An efficient sound speed estimation method to enhance image resolution in ultrasound imaging", available online Jul. 7, 2009. Ultrasonics, 49. pp. 774-778. (Year: 2009).*

Qu et al., "Average sound speed estimation using speckle analysis of medical ultrasound data", published online Apr. 28, 2012. Springer: Int J CARS, 7. pp. 891-899. (Year: 2012).*

Jaeger, Michael, et al. "Computed ultrasound tomography in echo mode for imaging speed of sound using pulse-echo sonography: proof of principle." Ultrasound in medicine & biology 41.1 (2015): 235-250.

U.S. Appl. No. 14/991,635, filed Jan. 8, 2016.

Office action in KR Patent Application No. 10-2017-0018294 dated Feb. 13, 2018, 19 pages (English translation attached).

White, P.J. et al:; "Longitudinal and shear mode ultrasound propagation in human skull bone"; Ultrasound in medicine & biology; vol. 32; No. 7; pp. 1085-1096.

Anderson, M. E. et al:; "The impact of sound speed errors on medical ultrasound imaging"; The Journal of the Acoustical Society of America; vol. 107; No. 6; pp. 3540-3548.

Deffieux, Thomas:; "Palpation par force de radiation ultrasonore et échographie ultrarapide: Applications à la caractérisation tissulaire in vivo."; Physique; Université Paris-Diderot—Paris VII 2021q02817.

* cited by examiner

SOUND SPEED IMAGING USING SHEAR WAVES

BACKGROUND

The present embodiments relate to speed of sound determination with ultrasound.

In ultrasound imaging, the speed of sound is assumed, such as assumed to be 1450 m/s. The delay or phase profiles for focusing ultrasound beams rely on the assumed speed of sound. The assumption may not be accurate. The speed of sound in tissue varies based on characteristics of the tissue.

Ultrasound tomography may be used to measure the speed of sound. Ultrasound tomography relies on placing the patient between a transmitter and a receiver. The travel time for acoustic energy from the transmitter to pass entirely through the patient to the receiver is used to calculate the speed of sound in the patient. Most ultrasound scanners use pulse-echo where the same transducer is used for transmit and receive operation, so speed of sound may not be estimated in the same way with pulse-echo systems. Since the location of acoustic reflection is not known exactly relative to the transducer, the pulse-echo round trip time does not directly indicate the speed of sound.

BRIEF SUMMARY

By way of introduction, the preferred embodiments described below include methods, computer readable media, and systems for sound speed imaging. Shear wave propagation is used to estimate the speed of sound in the patient. A pulse-echo ultrasound scanner detects a time of occurrence of a shear wave at each of multiple locations. The difference in time of occurrence, given tissue stiffness or shear velocity, is used to estimate the speed of sound.

In a first aspect, a method is provided for sound speed imaging. An ultrasound scanner transmits an acoustic radiation force impulse into tissue of a patient along a first line. The ultrasound scanner detects displacements over time of the tissue generated in response to a shear wave resulting from the acoustic radiation force impulse. The displacements are detected at each of at least two locations spaced from the first line. A change in time of the displacements over time for a first of the locations relative to the displacements over time a second of the locations is detected. The speed of sound in the patient is calculated from the change in time. An image of the speed of sound is generated.

In a second aspect, a system is provided for imaging speed of sound. A transmit beamformer is configured to generate an excitation pulse. A receive beamformer configured to detect responses of tissue to a shear wave generated by the excitation pulse. The responses are detected at each of a plurality of locations at each of a plurality of times. An image processor is configured to estimate the speed of sound in the tissue from the responses of the tissue to the shear wave. A display is operable to display the speed of sound.

In a third aspect, a non-transitory computer readable storage medium has stored therein data representing instructions executable by a programmed processor for estimating sound speed. The storage medium includes instructions for: observing a shear wave propagating in a medium with an ultrasound scanner, calculating a speed of sound in the medium as a function of (a) a shear velocity or stiffness and (b) a time difference for the shear wave to propagate to different positions in the medium, and transmitting the speed of sound.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The speed of sound is estimated and imaged using a shear wave. Using an acoustic radiation force impulse, the shear wave is generated. The tissue displacements from the shear wave are obtained for multiple locations with an ultrasound scanner and analyzed to estimate the speed of sound. In one embodiment, the speed of sound is estimated by observing a shear wave propagating in a medium. A known or pre-estimated stiffness or shear velocity is used with the shear wave propagation information to estimate the speed of sound.

Since the timing of shear wave displacement at different locations is determined, pulse-echo ultrasound may be used to estimate the speed of sound. Speed of sound may be diagnostically useful, such as correlating with a disease state more strongly than other measures (e.g., correlating more strongly than shear velocity or tissue stiffness).

Figure 1:
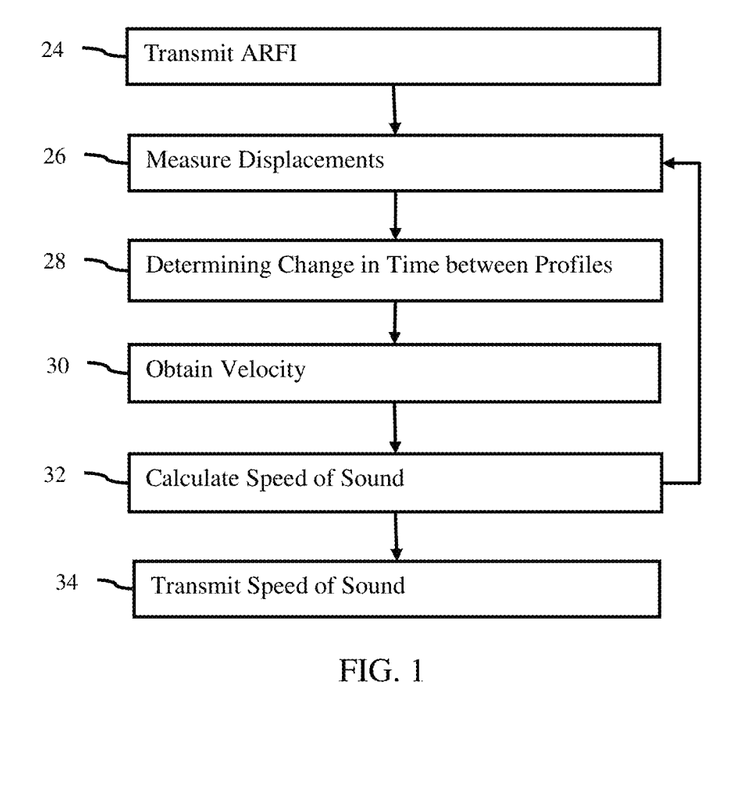
FIG. 1 is a flow chart diagram of one embodiment of a method for sound speed imaging.

FIG. 1 shows one embodiment of a method for sound speed imaging. An ultrasound scanner observes shear wave propagation in a medium. The speed of sound in that medium is calculated as a function of the shear velocity or tissue stiffness and a time difference for the shear wave to propagate to different positions in the medium. The locations sampled by an ultrasound scanner use an assumed or previously set speed of sound, so they are at an assumed distance apart. By tracking the shear wave, the actual distance between two locations is found based on a difference in time of occurrence of the shear wave at the locations. The ratio of this actual distance to the assumed distance is the same as the ratio of the actual speed to the assumed speed, so the actual speed may be calculated.

Figure 6:
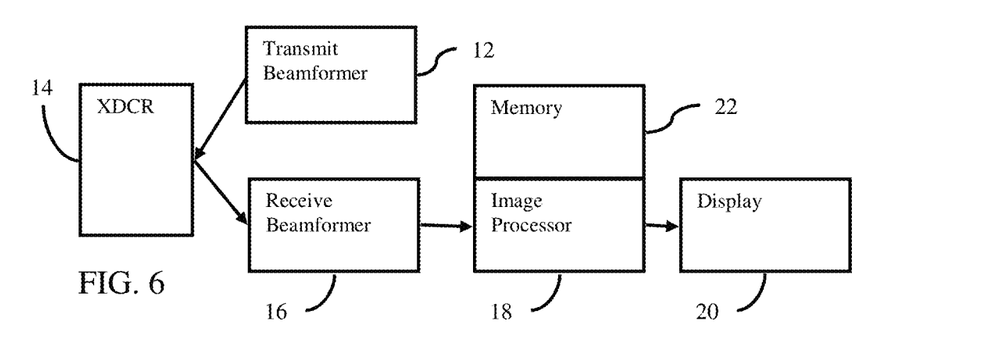
FIG. 6 is one embodiment of a system for estimating speed of sound in tissue.

The method is implemented by the system of FIG. 6 or a different system. For example, any now known or later developed ultrasound scanner performs all of the acts. A processor, controller, or image processor of the ultrasound scanner performs acts 28-32. Alternatively, a processor of a computer or workstation separate or remote from the ultrasound scanner performs any one or more of acts 28-32. Beamformers, memory, detectors, and/or other devices may be used to acquire the data using acts 24 and 26. The ultrasound scanner, image processor, display, or other device may perform act 34. The image processor may control the devices to perform the method of FIG. 1.

Additional, different, or fewer acts may be provided. For example, the method is performed without transmitting the speed in act 34. As another example, the shear wave is generated without an ARFI transmission of act 24. In yet another example, a default or assumed shear velocity or other tissue characteristic (e.g., stiffness) is used instead of calculating the velocity in act 30. In other examples, filtering or other data processing is applied to the displacements or calculated speeds over time and/or space.

The acts are performed in the order described or shown (e.g., top to bottom), but may be performed in other orders. For example, act 24 shows transmission of a single excitation pulse. Act 24, and the responsive acts 26, 28, and 32, may be repeated to measure over a larger region of interest. Acts 26, 28, and 32 may be repeated to measure over a larger region of interest or with more samples in response to a same shear wave. As another example, act 30 is performed prior to act 24, such as using ARFI imaging to determine the shear velocity in the tissue of interest before using ARFI to determine the speed of sound in that tissue of interest.

In act 24, an ultrasound scanner transmits an ARFI push into tissue of a patient. The transmission is a transmit beam focused at a depth or range of depths on a scan line. The focal depth is on the transmit scan line.

Figure 2:
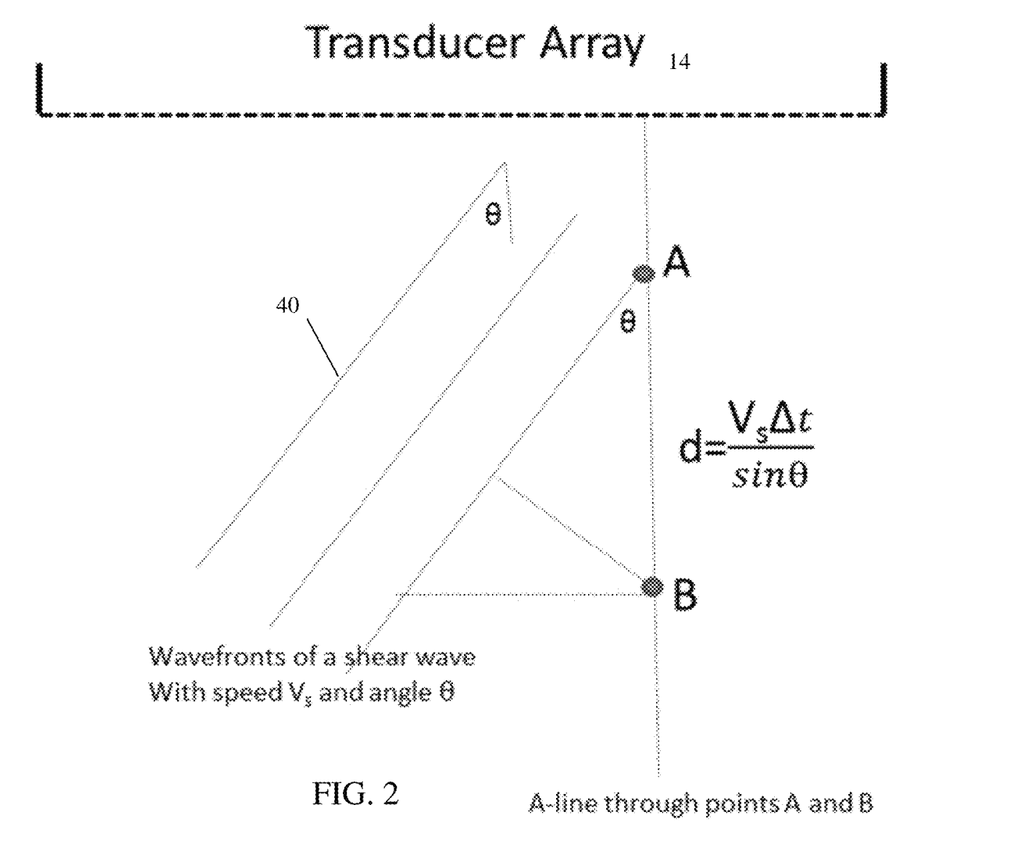
FIG. 2 illustrates an example arrangement of shear wave propagation to locations of displacement detection.

Based on a delay profile for the elements of the transducer, the ARFI transmit beam is transmitted along a transmit scan line. The scan line is at any angle to the transducer, such as normal to the transducer. An ARFI pulse is used to generate a shear wave that propagates at angle θ relative to the A-lines or detection scan lines in act 26. In one embodiment, the scan line for the ARFI transmit beam is at any angle within the field of view of the transducer, such as being within +/−30 degrees relative to normal to the transducer. FIG. 2 shows an example with the ARFI transmit scan line 40 at an angle θ of about 20 degrees from normal. The point of origin on the transducer is the center of the transducer, but may be offset from the center.

An array of elements in an ultrasound transducer transmits the ARFI beam converted from electrical waveforms. The acoustic energy is transmitted to the tissue in a patient. The acoustic waveform is transmitted as stress for generating a shear wave to displace tissue. The excitation is an ultrasound excitation pulse. The acoustic energy is focused to apply sufficient energy to cause generation of one or more waves that then travel through the tissue from the focal location. The acoustic waveform may itself displace the tissue. Other sources of stress may be used, such as a mechanical external force or an internal force.

To generate the wave, high amplitude or power excitations are desired. For example, the excitation has a mechanical index of close to but not exceeding 1.9 at any of the focal locations and/or in the field of view. To be conservative and account for probe variation, a mechanical index of 1.7 or other level may be used as the upper limit. Greater (e.g., MI exceeding 1.9) or lesser powers may be used.

The excitation pulse is transmitted with waveforms having any number of cycles. In one embodiment, one, most, or all of the waveforms for a pushing pulse transmit event have 100-2,000 cycles. The number of cycles is tens, hundreds, thousands, or more for the continuous transmit waveforms applied to the elements of the array for the excitation pulse. Unlike imaging pulses that are 1-5 cycles, the ARFI excitation or pushing pulse has a greater number of cycles to generate sufficient stress to cause the shear wave for displacing tissue with an amplitude sufficient to detect.

The shear wave is generated at the focal region and propagates laterally from the focal region. The shear wave travels perpendicular to the transmit scan line. In the example of FIG. 2, the shear wave travels at an angle greater than 0 degrees (e.g., greater than 20) and less than 90 degrees (e.g., less than 70) relative to the A-line or scan lines used to track the shear wave. In the specific example of FIG. 2, the angle is about 20 degrees. The locations A, B of tracking in act 26 are along a scan line normal to the array. The waves may travel in multiple directions. The waves reduce in amplitude as the waves travel through the tissue.

In one embodiment, a single excitation pulse is generated. In other embodiments, a pattern of excitation pulses may be generated. Any pre-determined pattern may be used, such as pulses overlapping in time but with different frequency, focus, or other characteristic. One example pattern is a sequence of excitations with a short pause between the pulses. The short pause may be less than a time for reverberation reduction and/or less than a length of an excitation pulse. The pattern provides different excitations prior to tracking in act 26. Because of the pattern, a series of shear waves are generated. This results in a pattern of waves and corresponding displacements at different locations. This pattern may be used to provide additional peaks or other information for estimating a speed.

In act 26, the ultrasound scanner measures or detects displacements of the tissue generated in response to the ARFI transmission. The response of tissue to the shear wave caused by the excitation is detected and used to measure the displacement.

The shear wave is generated in response to the ARFI transmission. The tissue response is a function of the wave created by the ARFI beam and the tissue characteristics. The wave is tracked at multiple locations. FIG. 2 represents the wave as parallel lines to the transmit scan line 40. For a shear wave, the wave travels perpendicularly to the transmit scan line 40, so the parallel lines are spaced perpendicularly to the transmit scan line 40. The locations A, B of tracking are along a receive scan line that is not parallel to the transmit scan line.

The generated wave is tracked. The tracking detects the effects of the wave rather than specifically identifying where the wave is located at a given time. The tracking is performed by ultrasound scanning. To detect the displacement, ultrasound energy is transmitted to the tissue undergoing displacement, and reflections of the acoustic energy are received. To detect tissue response to shear waves in a region of interest, transmissions are made to the region, and detection is performed in the region. These other transmissions are for detecting the waves or displacement rather than causing the wave or displacement. The transmissions for detection may have lower power and/or short pulses (e.g., 1-5 carrier cycles).

B-mode or other scanning along one or more receive lines is performed to track. The displacement indicates the effects of the wave, such as no displacement indicating an absence of the wave and a displacement indicating tissue movement caused by the wave. As the wave passes a given location, the tissue displaces by an amount or distance that increases to a peak amount and then decreases as the tissue returns to rest. Similarly, for a given time, one location may be displaced more than other locations since the peak of the wave is located at or by that location. The tracking may detect the effects of the wave at any stage (i.e., no wave, increasing displacement, maximum, or decreasing displacement).

The tissue is scanned multiple times to determine the displacement, such as scanning a region at least twice. To determine displacement at one time, a sample echo return is compared to a reference. The displacement is provided as the difference or offset from the reference scan (first scan) and a later scan (displacement measure). The tissue is scanned using any imaging modality capable of scanning for displacement during the tissue's response, such as during or after application of the ARFI excitation pulse.

For ultrasound scanning, the wave is detected at locations A, B adjacent to and/or spaced from the focal region for the ARFI excitation pulse. Any number of lateral locations may be used, such as two or more. The locations are along one or more receive scan lines. Non-parallel and/or non-vertical receive lines may be used. The transmissions for detection may have a wider beam profile along at least one dimension, such as laterally, for simultaneously forming receive samples along a plurality of scan lines (e.g., receive beamforming simultaneously along four or more receive lines). Any number of simultaneous receive beams may be formed, such as four, eight, sixteen, thirty-two, sixty-four, or more. In one embodiment, a parallel receive beamformer forms beams to sample the entire region of interest. Parallel beamformation is used to sample across the entire region of interest.

Some or all of the sample locations are at different depths. As shown in FIG. 2, the sample locations A, B are positioned so that the shear wave occurs at different times at the different locations. Sample locations at the same depth but different receive lines or other distributions of locations resulting in the shear wave passing at different times given the origin of the shear wave may be used.

The tracking transmissions and corresponding receive beams are performed sequentially. To sample over time, the tracking transmission and receiving of echoes from the multiple locations are repeated. The transmission and reception for detection or tracking are performed multiple times for each receive line to determine change due to displacement over time. Any transmission and reception sequence may be used.

For determining displacement, a reference scan of all of the receive lines in the region of interest is performed prior to the ARFI transmission of act 24. After the ARFI transmission of act 24, the tracking allows for measuring displacements per receive event. The samples or measured tissue responses are used to determine displacement in act 26.

The displacement is calculated from the ultrasound scan data. The tissue moves between two scans. A reference scan is performed before the ARFI transmit of act 24 and/or after the generated wave has passed the location. The data of the sample scan or the reference scan is translated or shifted in one, two, or three dimensions relative to the data in the other scan. For each possible relative position, an amount of similarity is calculated for data around the location. The amount of similarity is determined with correlation, such as a cross-correlation. A minimum sum of absolute differences or other function may be used. The spatial offset with the highest or sufficient correlation indicates the amount of displacement for a given location. In other embodiments, a phase offset of data received from different times is calculated. The phase offset indicates the amount of displacement. In yet other embodiments, data representing a line (e.g., axial) at different times is correlated to determine a shift for each of a plurality of depths along the line.

A single ARFI excitation pulse is used to estimate displacements for all the locations. By repeating the displacement detection using samples from the repeated tracking, the displacements for all of the locations are determined for each of multiple times (e.g., sampling every 0.1 ms over 0-7 ms). To monitor a larger region, excitation pulses and tracking may repeated for other locations.

Figure 3:
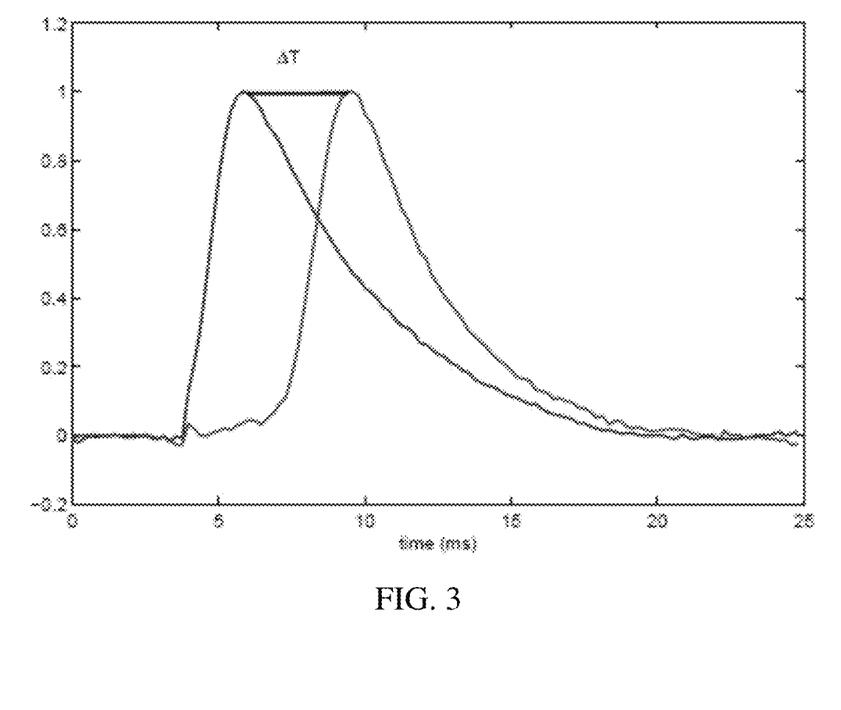
FIG. 3 shows two displacement profiles used to determine a change in time between occurrences of a shear wave.

Since time of maximum displacement for a given location is unknown, the sampled displacements may or may not be associated with a maximum displacement caused by the wave passing the tissue. FIG. 3 shows a graph of the displacements for each of two locations A, B as a function of time. The samples of displacement as a function of time for a given location are a displacement profile for that location. The profile generally starts with no shear displacement, ramps up to a peak in displacement representing occurrence of the shear wave, and then decays to the steady state of no displacement.

The same shear wave causes a peak in displacement to occur at different times for different locations. The difference in time between locations is a function of the distance between the locations, the velocity of the shear wave, and an angle.

FIG. 3 shows one peak for each location. Where a pattern of excitation pulses are used, multiple shear waves may be generated. Depending on whether the multiple excitation pulses have a same or different focal location, transmit scan line angle, and/or relative timing and the time being sampled, more than one peak may occur in the displacement as a function of time. The displacements caused by the pattern of waves are detected after the pattern of excitation pulses occurs (e.g., after the multiple shear waves are generated).

In act 28, an image processor determines a change in time of the displacements over time between any number of locations. The change in time for one location relative to another location is a time difference between occurrences of the shear wave at the locations. FIG. 3 shows the change in time as $\Delta T$. Coupled with the shear velocity and angle, this difference in time is used to determine an actual distance between the two sample locations A, B.

In one embodiment, the change in time is found from the displacement profiles. The peak is treated as the shear wave. The time of the peak indicates the time of occurrence of the shear wave at the location. Other parts of the profile may be used instead of the peak. The peak is identified as the maximum displacement over time. The measured displacements are compared to find the maximum. Alternatively, a curve is fit to the measured displacements, and the maximum of the fit curve is used. The peak displacement is identified for each of the displacement profiles (i.e., for each of the locations).

The difference in time is determined from the peak displacements. Each peak has a corresponding time. In the example of FIG. 3, the peak for location A occurs at time 5.8 ms, and the peak for location B occurs at time 9.6 ms. The difference in time is calculated from the times of occurrence of the peaks. In FIG. 3, $\Delta T$ is 3.8 ms.

In an alternative embodiment, the displacement profiles for the different locations are correlated. Different temporal shifts of the profile of one location relative to the profile of the other locations are attempted. The amount of correlation is calculated for each shift. The temporal shift with the greatest correlation provides the difference in time. Other approaches may be used.

With two locations, the difference in time is between the two peaks. Where a pattern of peaks is provided, such as due to transmitting the ARFI pulse with a defined wave front shape (i.e., pattern), the difference in time has a greater sampling. The differences between respective peaks of multiple peaks in each profile are determined. An average change in time is then found.

Where more than two locations are sampled, the difference in time may be found between different combinations of locations. This increases the sampling for a tissue region.

In act 30, the shear wave velocity or tissue stiffness is obtained. The value is obtained from memory or calculated from measurements. The velocity or stiffness in combination with change in time and angle may be used to derive the actual distance between the locations A, B. The velocity or stiffness is known a priori, obtained after act 26 (e.g., obtained in response to a different ARFI transmission), or obtained from the displacements also used to calculate the speed of sound.

The velocity or stiffness may be assumed. A default value (e.g., population average for the tissue of interest) is used. Alternatively, measures of displacement in the specific patient are used.

In one embodiment, the image processor determines the shear wave velocity by a distance from the shear wave origin to the sample location and a time of occurrence of the shear wave at the location. The displacement profile for a location laterally spaced from the ARFI focus is used. Different locations along a line perpendicular to the transmit scan line extending from the ARFI focal point may be used.

Various approaches to estimate shear velocity may be used. The velocity is calculated from the peak or peaks. Where a pattern of excitations and resulting waves are used, then more than one peak may be located for some or all of the times. This resulting pattern of peaks may be used to estimate the velocity of the shear wave.

In one embodiment, the calculation is simply the sample time for the peak and the distance of the location of the peak from the ARFI focal position. This calculation may be repeated for other times, providing velocities at different locations of peaks. Alternatively, the times of peaks from different locations are used to estimate a velocity for the tissue region or region of interest.

The velocity is alternatively calculated using phasing. The profiles of displacements as a function of time for different locations are correlated. The phase offset and the temporal sampling difference may be used to determine the velocity.

In another embodiment, the fitting is directly to a two-dimensional map of displacements without identifying peaks. The fitting may be weighted by the magnitudes of the displacements. The displacement magnitudes may be adjusted to account for wave attenuation as a function of distance before the displacement weighted fitting. Once fit, the line provides a slope or angle used to calculate the velocity. By using parallel beamforming across the entire region of interest, the resulting fit may be less susceptible to errors caused by physiological motion.

Where a pattern of waves is generated, the fitting may be different. For each time, multiple peaks are provided. The peaks may be distinguished from each other so that the different waves are separated. The pattern of wave generation (e.g., focal location and/or timing) is used to distinguish. Velocities for each wave are calculated separately. The resulting velocities may be combined. Alternatively, template patterns are matched or fit to the pattern of locations of peaks. The best-fit pattern is associated with a pre-determined velocity. Other approaches may be used, such as using a separation of the locations of peaks at a given time to indicate the velocity.

In one embodiment, tissue stiffness is used instead of or in addition to shear wave velocity. Any stiffness calculation may be used. For example, the stiffness is calculated from the shear wave speed by assuming an elastic and isotropic medium. The stiffness or Young's Modulus, E, is calculated as:

$$E = 3\rho V_s^2$$

where $\rho$ is density and $V_s$ is the shear velocity.

The calculation of shear wave velocity or tissue stiffness may use the displacements measured in act 26. The distance from the origin of the shear wave to the sample location may not be exact, but the resulting shear wave velocity or stiffness may be accurate enough. The speed of sound assumption may result in an inaccuracy in the beamformer-based distance between the ARFI focus and the sample location (e.g., location B).

Alternatively, displacements measured in response to a different shear wave are used. The displacements may be measured for locations other than the locations used to calculate the speed of sound.

In act 32, the image processor calculates the speed of sound. The speed of sound in the specific patient, specific tissue, and/or specific tissue location is calculated. The speed of sound between the sample locations A, B is calculated.

The speed of sound is calculated from the change in time from act 28 and the shear velocity or tissue stiffness of act 30. Since the shear wave velocity is known and the difference in time of occurrence of the shear wave at the different locations is measured, the actual distance between the locations may be determined. The ratio of the actual distance to the expected or beamformer-based distance indicates a weight for the expected speed of sound used by the beamformer to provide the actual speed of sound.

Referring to FIG. 2, the speed of sound is a function of the geometry related to travel of the shear wave to the locations. The speed of sound, c, is calculated from the change in time $\Delta T$, the angle $\theta$, the shear wave velocity $V_s$ or stiffness, the default speed of sound c' used by the beamformer, and the default distance d' between the sample locations given the default speed (i.e., the expected distance according to the beamforming or scan geometry). The actual distance, d, which is the component of the shear wave travel distance along the direction of the acquired A-line (i.e., along the receive scan line passing through A and B), is given by:

$$d = \frac{V_S \Delta T}{\sin \theta} \quad (1)$$

The default distance d' is based on the beamformer of the ultrasound scanner. The default speed c' is used by the beamformer to assign the sample locations. The default distance d' between the points A and B is given by:

$$d' = \frac{c' dt}{2} = \frac{\beta c dt}{2} = \beta d \quad (2)$$

where dt is the change in time or $\Delta T$ and $\beta$ is a ratio of c' and c.

$$\beta = \frac{c'}{c} \quad (3)$$

The ratio of the ultrasound scanner or default speed c' to the actual speed c is equal to the ratio of the ultrasound scanner or default distance d' to the actual distance d. The true or actual speed c is given by:

$$c = \frac{c'}{\beta} = \frac{dc'}{d'} \quad (4)$$

Since the distance d is determined from the results of acts 28 and 30 and the angle of the shear wave propagation relative to a line passing through the two sample locations is known from the scan geometry, the actual speed is determined.

Where more than two sample locations are used, the detection of act 26, determination of act 28, and calculation of act 32 may be repeated. The same shear wave and same shear wave velocity are used in the repetitions. Alternatively, the displacements for all of the locations are measured using parallel beamforming or beamforming along a single line, so act 26 is not repeated. In other alternatives, the shear velocity is different for different pairs of locations, so act 30 is repeated as well.

By repeating the calculation of speed of sound for different sets of locations, the increased sampling may be used so that an average speed is more accurate. In another embodiment, the repetition provides values for the speed of sound at each of different locations or regions. A one, two, or three-dimensional map of measures of speed of sound are provided. The speed of sound is different for different tissue and/or tissue with different characteristics.

In act 34, the image processor transmits the calculated speed or speeds. The transmission is to another component of the ultrasound system or out of the ultrasound system. For example, the speed is transmitted to a memory, beamformer, display, and/or network.

An image of the speed of sound may be generated and provided to the display. The image includes the speed as text, such as an alphanumeric representation. In one embodiment, a single speed of sound is determined. A user positions a pointer on an image. In response, the ultrasound scanner outputs a speed of sound calculated for that point. A graph, color-coding, intensity, or other modulation by speed may be used. Alternatively, the image includes a spatial distribution of speeds of sound for different locations. A one, two, or three-dimensional representation of speed as a function of location is rendered to the display. The display grid may be different from the scan grid and/or grid for which displacements are calculated. Color, brightness, luminance, hue, or other characteristic of pixels is modulated as a function of the speed of sound. Variation in speed by region may be visualized.

In another example, the speed is transmitted to a beamformer. The speed is transmitted to the beamformer controller, receive beamformer, and/or transmit beamformer. Alternatively, the speed is used to determine a delay or phase profile, and the profile is transmitted to the beamformer. Using the actual speed of sound or speeds of sound, the focusing and scan format of the beamformer is controlled to increase resolution or for more accurate scanning.

Figure 4A:
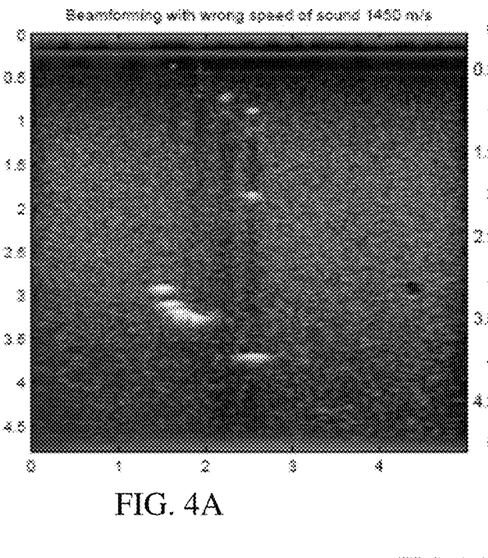
FIGS. 4A and 4B show example B-mode imaging with an assumed speed of sound and with a correct speed of sound, respectively.
Figure 4B:
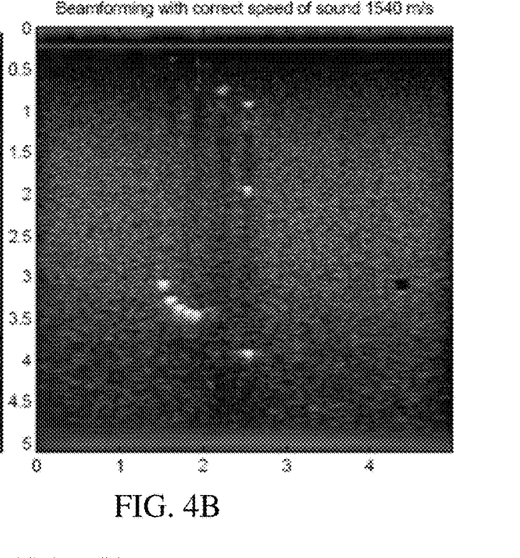

FIGS. 4A and 4B show examples using assumed and actual speed of sound in the beamforming of an ultrasound scanner for imaging a phantom with various point or line reflectors (bright spots). B-mode images are generated, but other types of imaging may be used. In FIG. 4A, the speed of sound is assumed to be 1450 m/s. In FIG. 4B, the actual speed of sound of 1540 m/s is used. The point or line reflectors are more defined or less blurry in FIG. 4B. Using the actual speed of sound may improve a sonographer's ability to distinguish anatomy and/or tissue state, helping with diagnosis. The actual speed of sound also results in more reliable distance indication. Note that the depth range from the transducer (0 cm) to the farthest depth in FIG. 4A is less than in FIG. 4B due to compression of the distance by the inaccurate speed of sound.

Figure 5:
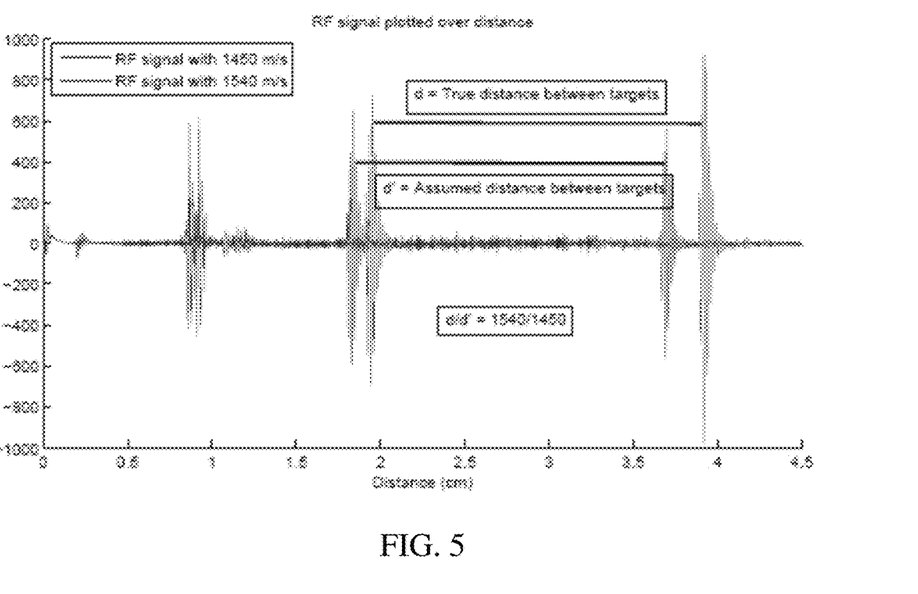
FIG. 5 illustrates example radio frequency signals output by a beamformer with the assumed and correct speeds of sound.

FIG. 5 is a plot of the beamformed samples or radio frequency data from about 2.5 cm along the x-axis of both FIGS. 4A and 4B. The radio frequency data represents echo response from three reflectors along this vertical line in FIGS. 4A and 4B. As a result, FIG. 5 shows three instances of increased signal intensity for each of the two radio frequency signals. Due to the use of assumed speed of sound, the three instances of increased intensity for FIG. 4A occur closer to the transducer and with less distance between the instances. Using the correct speed of sound alters the distance, providing a true distance between the points.

FIG. 6 shows one embodiment of a system for imaging speed of sound. By gathering scan data responsive to the tissue responding to shear wave displacement, the speed of sound is determined.

The system is a medical diagnostic ultrasound imaging system. In alternative embodiments, the system is a personal computer, workstation, PACS station, or other arrangement at a same location or distributed over a network for real-time or post acquisition imaging.

The system implements the method of FIG. 1 or other methods. The system includes a transmit beamformer 12, a transducer 14, a receive beamformer 16, an image processor 18, a display 20, and a memory 22. Additional, different, or fewer components may be provided. For example, a user input is provided for manual or assisted designation of a region of interest for which information is to be obtained.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing. The waveforms are generated and applied to elements of the transducer 14 with any timing or pulse repetition frequency. For example, the transmit beamformer 12 generates an excitation pulse for generating a shear wave in a region of interest and generates corresponding transmissions for tracking resulting displacements with ultrasound. The transmit beamformer 12 may be configured to generate a sequence or other combination of excitation pulses for generating multiple waves to be tracked.

The transmit beamformer 12 connects with the transducer 14, such as through a transmit/receive switch. Upon transmission of acoustic waves from the transducer 14, one or more beams are formed during a given transmit event. The beams are excitation pulses and/or tracking beams. For scanning tissue displacement, a sequence of transmit beams are generated to scan a one, two or three-dimensional region. Sector, Vector®, linear, or other scan formats may be used. The scanning by the transmit beamformer 12 occurs after transmission of the excitation pulse (i.e., ARFI pushing pulse), but may include scanning for reference frames used in tracking before transmitting the excitation pulse. The same elements of the transducer 14 are used for both scanning and displacing tissue, but different elements, transducers, and/or beamformers may be used.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms and connects with the receive beamformer 16 for converting acoustic echoes into electrical signals. The transducer 14 transmits the excitation pulse and tracking beams. The waveforms are focused at a tissue region or location of interest in the patient. The transmit beams are angled relative to the transducer at any of various angles within a field of view of the transducer 14. The acoustic waveforms are generated in response to applying the electrical waveforms to the transducer elements. For scanning with ultrasound to detect displacement, the transducer 14 transmits acoustic energy and receives echoes. Receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection of the tissue response or tracking. Dynamic focusing on receive may be provided. Where only one depth or depth range is of interest, dynamic focusing may or may not be provided. The receive beamformer 16 outputs data representing spatial locations using the received acoustic signals. Relative delays and/or phasing and summation of signals from different elements provide beamformation. In alternative embodiments, the receive beamformer 16 is a processor for generating samples using Fourier or other transforms.

For parallel receive beamformation, the receive beamformer 16 is a parallel receive beamformer configured to include additional sets of channels and corresponding summers. Each channel applies relative delays and/or phasing to from a beam with the summer. The receive beamformer 16 may have any number N of sets of channels and summers. N is an integer of 1 or greater, for forming a corresponding number of beams simultaneously or in response to a same tracking transmit beam. The receive beams may be formed as a regular sampling of space in a region of interest. The locations are simultaneously sampled by respective receive beams formed by the receive beamformer 16.

The receive beamformer 16 may include a filter, such as a filter for isolating information at a second harmonic or other frequency band relative to the transmit frequency band. Such information may more likely include desired tissue, contrast agent, and/or flow information.

The receive beamformer 16 outputs beam summed data representing spatial locations. Data for a single location, locations along a line, locations for an area, or locations for a volume are output. The data may be for different purposes. For example, different scans are performed for B-mode or tissue detection than for shear or longitudinal wave detection. Alternatively, the B-mode data is also used to determine displacement caused by a shear or longitudinal wave.

The receive beamformer 16 is configured to detect responses of tissue to the wave generated by the excitation pulse. The tissue is scanned. The receive signals generated by the receive beamformer 16 represent response from the tissue at the time of sampling. Different locations are sampled simultaneously. Since the tissue is subject to any displacement caused by the wave, the tissue response is captured by the sampling. The acoustic responses are detected at each of a plurality of locations at each of a plurality of times. The responses of the tissue to more than one wave may be detected. The receive beamformer 12 detects response of tissue to a shear wave at each of a plurality of locations at each of a plurality of times.

The image processor 18 or a separate beamformer controller configures the beamformers 12, 16. By loading values into registers or a table used for operation, the values of acquisition parameters used by the beamformers 12, 16 for ARFI or other imaging are set. The values include delay or phase profiles that rely on the speed of sound. For a given scan, the transmit beamformer 12 and/or the receive beamformer 16 use a given or default speed of sound. Any control structure or format may be used to establish the imaging. The beamformers 12, 16 are caused to acquire data for imaging at a frame rate and/or with a resolution. Different values of one or more acquisition parameters may result in a different frame rate and/or resolution.

The image processor 18 is a B-mode detector, Doppler detector, pulsed wave Doppler detector, correlation processor, Fourier transform processor, application specific integrated circuit, general processor, control processor, field programmable gate array, digital signal processor, analog circuit, digital circuit, combinations thereof or other now known or later developed device for calculating displacements from responses output by the receive beamformer 16, calculating shear velocity, calculating differences in time, and/or calculation speed of sound.

In one embodiment, the image processor 18 includes one or more detectors and a separate processor. The separate processor is a control processor, general processor, digital signal processor, graphics processing unit, application specific integrated circuit, field programmable gate array, network, server, group of processors, data path, combinations thereof or other now known or later developed device for determining displacement and/or calculating speed of sound from displacements. The processor 18 is configured by software and/or hardware to perform the acts.

In one embodiment for speed of sound imaging, the processor 18 estimates tissue displacement for each of a plurality of lateral locations over time. The displacements occurring at different times are estimated for each location. For example, estimates of displacements for the various locations are formed for each of multiple sample times. The data output by the receive beamformer 16 is used to determine the displacements at each location for each of different times. The displacements may be obtained by correlating or otherwise determining level of similarity between reference data and data obtained to represent the tissue at a time.

The image processor 18 may be configured to estimate the shear wave velocity or other characteristic of tissue from the displacements used for calculating speed of sound or displacements measured in response to a different shear wave. One or more peaks in a profile of the displacements as a function of time are found. Based on the distance from the excitation pulse focal point to the sample location and the time of occurrence of the shear wave at the sample location, the image processor 18 calculates the shear wave velocity. In another example, the processor 18 calculates tissue stiffness, viscosity, and/or modulus. The processor 18 may calculate other properties, such as strain or elasticity. In alternative embodiments, an assumed or default value of the shear wave velocity is used instead of a measured value.

The image processor 18 is configured to estimate the speed of sound in the tissue from the responses of the tissue to the shear wave. The speed of sound is estimated from the displacements. The displacements over time for each location are compared to find a difference in time of occurrence of the shear wave at the locations. Where the transmit line for the shear wave is not parallel to a line through the sample locations, the shear wave arrives or passes by each of the locations at a different time. The angle for the transmit scan line for the ARFI to the line through the sample locations, the difference in time, and the velocity of the shear wave are used to calculate the actual distance between the sample locations. The beamformer-based speed of sound and distance between the locations are used with the actual distance to calculate the speed of sound. The ratio of the actual distance to the beamformer distance is equal to the ratio of the actual speed of sound to the beamformer speed of sound, allowing the image processor 18 to calculate the speed of sound.

The speed of sound is estimated for one location, such as a user designated location. Alternatively, the speed of sound is estimated for each of a plurality of locations. The image processor 18 determines a spatial distribution of speeds of sound in the patient.

The processor 18 generates and outputs image or display values mapped from the speed of sound to the display 20. A text or numerical indication of the speed of sound is displayed to the user. In one embodiment, the speed of sound is displayed as a function of location. Values, graphs, and/or tissue representations may be displayed using the speed at different locations. For a representation of the tissue, the speed of sound modulates the color, hue, brightness, and/or other display characteristic for different pixels representing a tissue region. The image processor 18 determines a pixel value (e.g., RGB) or a scalar value converted to a pixel value. The image is generated as the scalar or pixel values. The image may be output to a video processor, look-up table, color map, or directly to the display 20.

The display 20 is a CRT, LCD, monitor, plasma, projector, printer, or other device for displaying an image or sequence of images. Any now known or later developed display 20 may be used. The display 20 is operable to display one image or a sequence of images. The display 20 displays two-dimensional images or three-dimensional representations. The display 20 displays one or more images representing the speed of sound derived from shear wave-caused displacements. A table, patient report, or tissue representation is displayed with the speed included. As another example, a speed of sound associated with a location indicated on a two-dimensional image or three-dimensional B-mode representation is displayed. Alternatively or additionally, the image is a graph. In yet other embodiments, a B-mode image overlaid with color modulation for speed of sound is displayed.

The image processor 18 may transmit the speed of sound to the transmit beamformer 12, the receive beamformer 16, or both. The transmission to the beamformers 12/14 may be to a beamformer controller. The speed of sound value itself or the speed of sound as incorporated into delay/phase profiles based on the speed of sound are transmitted. The beamformers 12, 14 are configured to scan using delay and/or phase profiles based on the speed of sound. Using the measured or actual speed of sound for the tissue of the patient to configure the beamformers 12, 14 may result in more accurate spatial representation. The estimated speed of sound is used for operating the beamformers 12, 14 in a subsequent scan of any type (e.g., B-mode imaging). The speed is estimated once for a given imaging session. In other embodiments, the speed is periodically estimated throughout an imaging session for a patient.

The processor 18, the receive beamformer 16, and the transmit beamformer 12 operate pursuant to instructions stored in the memory 22 or another memory. The instructions configure the system for performance of the acts of FIG. 1. The instructions configure the image processor 18, the receive beamformer 16, and/or the transmit beamformer 12 for operation by being loaded into a controller, by causing loading of a table of values, and/or by being executed. The transmit beamformer 12 is configured by the instructions to cause generation of an excitation beam, tracking beams, and/or other imaging beams. The receive beamformer 16 is configured by the instruction to acquire data for tracking and/or imaging. The image processor 18 is configured to estimate displacements and speed of sounds from the displacements.

The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for sound speed imaging, the method comprising:
    transmitting, with an ultrasound scanner, an acoustic radiation force impulse into tissue of a patient along a first line;
    detecting, with the ultrasound scanner, displacements over time of the tissue generated in response to a shear wave resulting from the acoustic radiation force impulse, the displacements being detected at each of at least two locations spaced from the first line;
    determining a change in time of the displacements over time for a first of the locations relative to the displacements over time for a second of the locations;

calculating a speed of sound in the patient from the change in time, an angle, a shear wave velocity, a default speed, and a distance between the locations given with the default speed; and generating an image of the speed of sound.

2. The method of claim 1 wherein transmitting comprises transmitting where the acoustic radiation force impulse is focused at a depth along the first line, and wherein detecting comprises detecting with at least one of the locations being at a different depth than the depth along the first line and with the locations being along a second line different than the first line.

3. The method of claim 1 wherein transmitting comprises transmitting with the first line being at the angle away from normal to a transducer, and wherein detecting comprises detecting with the locations along a second line at a different angle relative to the transducer than the first line.

4. The method of claim 1 wherein detecting the displacements over time comprises detecting a displacement profile for each of the locations.

5. The method of claim 1 wherein detecting the displacements comprises determining an amount of shift of tissue from a reference.

6. The method of claim 1 wherein determining comprises identifying peak displacements in the displacements over time for each of the locations and determining a difference in time between the peak displacements.

7. The method of claim 1 wherein determining comprises correlating the displacements over time of a first of the locations with the displacements over time of a second of the locations.

8. The method of claim 1 wherein calculating the speed of sound comprises calculating the speed of sound in the patient between the locations; and further comprising repeating the detecting, determining, and calculating for other sets of locations responsive to the shear wave;

wherein generating the image comprises generating an image of a spatial distribution of the speeds of sound for the patient for the sets of locations.

9. The method of claim 1 further comprising estimating the shear wave velocity in the patient;

wherein calculating the speed of sound comprises calculating a distance from the change in time and the shear wave velocity, and calculating the speed of sound from the distance from the change in time and the shear wave velocity.

10. The method of claim 1 wherein the shear wave travels at the angle, the angle being greater than 20 degrees and less than 70 degrees to a line through the locations.

11. The method of claim 1 wherein generating the image comprises generating an image showing a value of the speed of sound.

12. The method of claim 1 further comprising using the speed of sound in a beamformer of the ultrasound scanner for imaging the patient.

13. The method of claim 1 wherein transmitting comprises transmitting the acoustic radiation force impulse as one impulse in a pattern of multiple impulses with the detecting being performed in response to the pattern, and wherein determining comprises determining the change in time from multiple peaks in the displacements for each location.

14. A system for imaging speed of sound, the system comprising:

a transducer;

a transmit beamformer configured to cause the transducer to generate an ultrasound excitation pulse in a patient;

a receive beamformer configured to detect, with ultrasound received by the transducer, responses of tissue to a shear wave generated by the excitation pulse, the responses detected at each of a plurality of locations in the patient at each of a plurality of times;

an image processor configured to estimate the speed of sound in the tissue from the responses of the tissue to the shear wave, the speed of sound estimated from (a) a ratio of actual distance, which is given by difference in time of shear wave occurrence, to assumed distance being equal to the ratio of the speed of sound to assumed speed, (b) a weight based on an actual distance given by a shear wave velocity and a change in time related to the shear wave being applied to an expected speed, or (c) a change in time related to the shear wave, an angle, the shear wave velocity or tissue stiffness, a default speed of sound, and a default distance; and a display configured to display an image representing the speed of sound in the patient.

15. The system of claim 14 wherein the image processor is configured to estimate the speed of sound as a function of a distance and configured to calculate the distance from a measure of shear velocity in the tissue and a difference in time of the shear wave passing the locations, the difference in time being the change in time related to the shear wave.

16. The system of claim 14 wherein the image processor is configured to estimate the speed of sound at the locations, and wherein the display is configured to display the speeds of sound at the plurality of the locations in the image.

17. The system of claim 14 wherein the transmit beamformer, receive beamformer or both the transmit beamformer and receive beamformer are configured to scan with delay profiles based on the estimated speed of sound.

18. A method for sound speed imaging, the method comprising:

transmitting, with an ultrasound scanner, an acoustic radiation force impulse into tissue of a patient along a first line;

detecting, with the ultrasound scanner, displacements over time of the tissue generated in response to a shear wave resulting from the acoustic radiation force impulse, the displacements being detected at each of at least two locations spaced from the first line;

determining a change in time of the displacements over time for a first of the locations relative to the displacements over time for a second of the locations;

calculating a speed of sound in the patient from the change in time, the calculating of the speed of sound being based on a first ratio of an ultrasound system used speed to the speed of sound being equal to a second ratio of an ultrasound system-based distance between the locations and a shear wave-based distance, the shear wave-based distance being a function of the change in time; and generating an image of the speed of sound.

19. A non-transitory computer readable storage medium having stored therein data representing instructions executable by a programmed processor for estimating sound speed, the storage medium comprising instructions for:

observing a shear wave propagating in a medium with an ultrasound scanner;

calculating a speed of sound in the medium as a function of a default speed, an angle of propagation of the shear wave relative to a line passing through different positions in the medium, and a distance determined from (a)

a shear velocity or stiffness and (b) a time difference for the shear wave to propagate to the different positions in the medium; and generating an ultrasound image with the ultrasound scanner using the calculated speed of sound or displaying an image of a spatial distribution as a one, two, or three dimensional representation of the speed of sound as a function of location in the medium.

\* \* \* \* \*